(12) United States Patent
Hauck et al.

(10) Patent No.: US 9,398,866 B2
(45) Date of Patent: Jul. 26, 2016

(54) SYSTEM FOR DETERMINING THE POSITION OF A MEDICAL DEVICE WITHIN A BODY

(71) Applicant: St. Jude Medical, Atrial Fibrillation Divsion, Inc., St. Paul, MN (US)

(72) Inventors: John A. Hauck, Shoreview, MN (US); Graydon E. Beatty, Bloomington, MN (US); Kevin Dillon, Chanhassen, MN (US); Mark A. MacGregor, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 13/959,839

(22) Filed: Aug. 6, 2013

(65) Prior Publication Data

US 2014/0031640 A1 Jan. 30, 2014

Related U.S. Application Data

(62) Division of application No. 12/981,150, filed on Dec. 29, 2010, now Pat. No. 8,517,031.

(51) Int. Cl.
*A61B 5/06* (2006.01)
*A61B 5/0408* (2006.01)
*A61B 5/042* (2006.01)
*A61B 5/00* (2006.01)

(52) U.S. Cl.
CPC ............... *A61B 5/065* (2013.01); *A61B 5/063* (2013.01); *A61B 5/6869* (2013.01); *A61B 5/0422* (2013.01); *A61B 5/04085* (2013.01); *A61B 5/6833* (2013.01); *A61B 2034/2053* (2016.02)

(58) Field of Classification Search
CPC ...... A61B 5/063; A61B 5/065; A61B 5/6869; A61B 5/6832; A61B 5/6833; A61B 5/04087; A61B 19/5244; A61B 2019/5246; A61B 2019/5251; A61B 2019/5253; A61B 2019/5272
USPC ........................... 128/899; 600/407, 409, 424
See application file for complete search history.

(56) References Cited

U.S. PATENT DOCUMENTS

| 4,448,199 A | 5/1984 | Schmid |
| 5,697,377 A | 12/1997 | Wittkampf |

(Continued)

FOREIGN PATENT DOCUMENTS

| EP | 2204120 | 7/2010 |
| WO | 2006/079888 | 8/2006 |
| WO | 2008/032291 | 3/2008 |

OTHER PUBLICATIONS

"Partial European Search Report", EP 11180941.4.

*Primary Examiner* — Charles A Marmor, II
*Assistant Examiner* — Carrie R Dorna
(74) *Attorney, Agent, or Firm* — Dykema Gossett PLLC

(57) ABSTRACT

A system for determining a position of a medical device within a body is provided that reduces positional error by establishing a reference origin closer to the device and/or simplifies the system by integrating components and functions. In one embodiment, a pair of drive electrodes are affixed to opposed surfaces of the body and create a pathway for transmission of current through a position sensor related to the medical device. A pair of reference electrodes proximate the drive electrodes are coupled to a common reference node outputting a reference signal establishing the reference origin. An electronic control unit determines the position of the medical device responsive to the position signal and the reference signal. In another embodiment, a patch affixed to an external surface of the body has a base layer and multiple devices supported on the base layer, electrically isolated from one another, and configured to perform different functions.

18 Claims, 5 Drawing Sheets

(56) References Cited

U.S. PATENT DOCUMENTS

| | | | |
|---|---|---|---|
| 6,050,267 A | 4/2000 | Nardella et al. | |
| 6,618,612 B1 * | 9/2003 | Acker et al. | 600/424 |
| 7,263,397 B2 | 8/2007 | Hauck et al. | |
| 2007/0060833 A1 | 3/2007 | Hauck | |
| 2008/0161669 A1 * | 7/2008 | Hauck et al. | 600/374 |
| 2008/0221425 A1 * | 9/2008 | Olson et al. | 600/407 |
| 2009/0264739 A1 | 10/2009 | Markowitz, II et al. | |

* cited by examiner

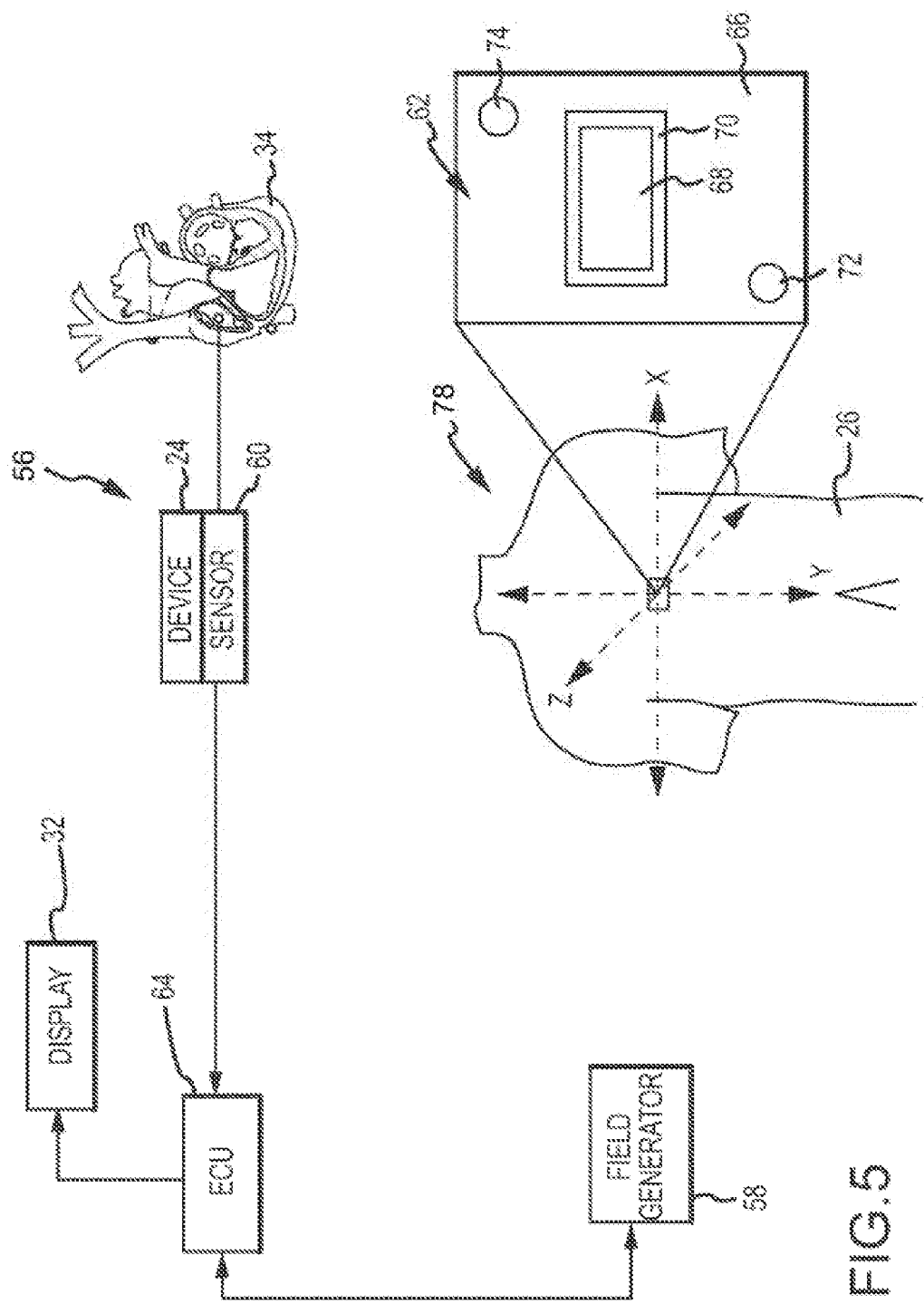

SYSTEM FOR DETERMINING THE POSITION OF A MEDICAL DEVICE WITHIN A BODY

CROSS-REFERENCE TO RELATED APPLICATIONS

This application is a divisional of U.S. application Ser. No. 12/981,150, filed 29 Dec. 2010, now pending, which is hereby incorporated by reference as though fully set forth herein.

BACKGROUND OF THE INVENTION a. Field of the Invention

This invention relates to a system for determining the position of a medical device within a body. In particular, the invention relates to a system that establishes a reference origin of a position coordinate system nearer the medical device to reduce errors in position measurements and that may also simplify the system by integrating components and functions of the system.

b. Background Art

It is desirable to track the position of medical devices as they are moved within a body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and clinician to undesirable levels of electromagnetic radiation. As a result, medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a clinician through, for example, a visual display.

One conventional medical device navigation system is offered for sale under the trademark "ENSITE NAVX™" by St. Jude Medical, Inc. The system is based on the principal that when electrical currents are passed through the thorax a voltage drop occurs across internal organs such as the heart and this voltage drop can be measured and used to determine the position of a medical device within the body. The system includes three pairs of patch electrodes that are placed on opposed surfaces of the body (e.g., chest and back, left and right sides of the thorax, and neck and leg) and form generally orthogonal x, y, and z axes as well as a reference electrode that is typically placed near the stomach and provides a reference value and acts as the origin of the coordinate system for the navigation system. Sinusoidal currents are driven through each pair of patch electrodes and voltage measurements for one or more electrodes associated with the medical device are obtained. The measured voltages are proportional to the distance of the device electrodes from the patch electrodes. The measured voltages are compared to the potential at the reference electrode and a position of the device electrodes within the coordinate system of the navigation system is determined. Referring to FIG. 1, the inventors herein have identified a simplified zero-order circuit 10 that illustrates the system for any given axis. Although the following description refers to impedances within circuit 10, only the real or resistive portion of a given impedance is used. In the illustrated circuit 10, the medical device within the body includes three electrodes represented by impedances $12_1$, $12_2$, $12_3$. Amplifiers, filters and other signal processing circuitry for each electrode create impedances $14_1$, $14_2$, $14_3$. The position of each electrode along the axis is determined responsive to the voltage at nodes $16_1$, $16_2$, $16_3$ which, when divided by the drive current, will yield resistances. The resistance generated by the body is represented by resistance 20, denoted as $R_b$. The position (P) of an electrode along an axis may be obtained using the following equation (1):

$$P = \frac{S_f * R_b * R_i}{R_i + R_e}$$

where $R_e$ is the resistance of the individual electrode (typically 100-500 ohms, but may exceed 1000 ohms with specialty electrodes), $R_i$ is the input resistance of the amplifier (typically 200-1000 kilo ohms), $S_f$ is a scale factor (e.g., 25 mm/ohm), and $R_b$ is the resistance of the body along the axis (typically 5-30 ohms).

The above-described system can be used to provide a substantially accurate indication of the position of the medical device. As indicated in the above-recited formula, however, the position determination along each axis is generally proportional to the resistance Rb of the body between the anatomical region of interest and the reference electrode. This resistance Rb varies along each axis. The varying body resistance Rb contributes to a variety of position measurement errors including: (1) drift resulting from a changing position of the medical device over time relative to the original measured position; (2) shift resulting from a change to certain parameters (e.g., connection or disconnection of the medical device or movement of the reference electrode); (3) scatter resulting from variation of electrode impedances or the amplifiers and related circuitry; and (4) offset resulting from differences in impedance among the electrodes and amplifiers and related circuitry among multiple catheters. For example, in one realistic scenario the body resistance Rb between the location of the reference electrode and the anatomical region of interest may be 12 ohms with an input resistance Ri along the sense amplifier channel of 200 kilo ohms and a scale factors Sf of 25 mm/ohm. In the case of a specialty electrode having a nominal resistance Re of 2 kilo ohms, the resistance may vary within a range of +/−30%, or between 1.4 and 2.6 kilo ohms. If electrodes having 1.4 and 2.6 kilo ohms are placed at an identical location, the position of the electrode along the axis calculated using equation (1) would yield different results at 297.9 millimeters and 296.2 millimeters, respectively—a difference of 1.7 millimeters. In the case where multiple electrodes are separate by, for example, 5 millimeters on a catheter, 1 deviation of 1.7 millimeters about a mean along any of the three axes will result in a visible error. A linear catheter may be erroneously depicted with electrode locations creating a saw tooth pattern instead of a smooth pattern. As another example, the body resistance Rb may change over time due to, for example, a saline infusion received by a patient which will generally lower body resistance. If the initial body resistance Rb is again 12 ohms, a 2% reduction in Rb would change the 297.9 millimeter position location of the electrode referred to above to 291.9 millimeters—a 6 millimeter drift.

The use and placement of the reference electrode is also disadvantageous because clinicians are required to locate and place a separate electrode and facilities must likewise maintain an inventory of the electrodes. Medical device navigation systems employ special purpose electrodes, sensors and other components that are separately connected to the body surface.

Oftentimes, these systems are used simultaneously with, and even cooperatively with, other systems employing different electrodes and sensors that are also connected to the body surface. For example, electrocardiography (ECG) electrodes are typically connected to the body during the same procedures in which navigation systems are used in order to monitor critical vital signs and as an input to the navigation system to compensate for motion of the heart. Similarly, magnetic navigation systems typically employ a sensor to monitor movement of the patient in order to compensate for this movement in determining the position of the medical device. The proliferation of electrodes, sensors and other components connected to the body increases the chance of error in setting up the various systems and increases the time required to prepare and complete a procedure.

The inventors herein have recognized a need for a system for determining the position of a medical device within a body that will minimize and/or eliminate one or more of the above-identified deficiencies.

BRIEF SUMMARY OF THE INVENTION

It is desirable to provide a system for determining the position of a medical device within a body. In particular, it is desirable to provide a system that will reduce errors in position measurements by establishing a reference origin for a coordinate system of the positioning system nearer the medical device to reduce the impact of body resistance and/or to simplify the system by integrating components and functions of the system.

A system in accordance with one embodiment of the invention for determining a position of a medical device within a body, the system defining a coordinate system, includes first and second drive electrodes. The first and second drive electrodes are configured to be affixed to opposed external surface of the body so as to create a first pathway for transmission of current through the body and thereby generate a voltage on a device electrode having a known positional relationship to the medical device. The system further includes first and second reference electrodes disposed proximate the first and second drive electrodes, respectively. The first and second reference electrodes and coupled to a common reference node. The common reference node outputs a reference signal establishing an origin of the coordinate system. An electronic control unit is configured to determine the position of the medical device responsive to a position signal generated by the device electrode and the reference signal.

A system in accordance with the above-described embodiment of the present invention is advantageous because it establishes a virtual reference electrode nearer to the medical device and more centrally located relative to axes on which currents are transmitted. As a result, body resistance between the medical device and the reference electrode is reduced or eliminated and measurement position errors resulting from drift, shift, scatter and offset are likewise reduced or eliminated. With reference to the example described above, for example, a reduction in the body resistance $R_b$ from 12 ohms to 1.2 ohms will cause a corresponding order of magnitude reduction in the potential measurement errors. Thus, the 1.7 millimeter deviation resulting from the different resistance values of the electrodes becomes 0.17 millimeters. Similarly, the 6 millimeter drift resulting from variations in body resistance over time becomes 0.6 millimeters. As a result, the potential errors are brought within clinically acceptable measures.

A system in accordance with another embodiment of the invention for determining a position of a medical device within a body, the system defining a coordinate system, includes a field generator and a position sensor generating a position signal indicative of a position of the medical device in the coordinate system. One of the field generator and the position sensor is disposed outside of the body and another of the field generator and the position sensor has a known positional relationship to the medical device. The system further includes a patch comprising a flexible and unitary base layer configured for attachment to an external surface of the body. The patch further includes a first device supported on the base layer and configured to perform a first function and a second device supported on the base layer and configured to perform a second function different from the first function. In one embodiment of the invention, for example, one of the devices comprises an electrode configured to establish an electrical pathway with another electrode disposed on an opposed surface of the body while the other device comprises an electrode configured to output a reference signal against which the position signal is compared. The second device is electrically isolated from the first device. The system further includes an electronic control unit configured to determine the position of the medical device responsive to the position signal and an output of at least one of the first and second devices.

A system in accordance with above-described embodiment of the invention is advantageous relative to conventional systems because it integrates component and/or functions that require separate components in conventional systems. As a result, fewer components are required for procedures thereby reducing inventory and procedural time and complexity.

The foregoing and other aspects, features, details, utilities and advantages of the present invention will be apparent from reading the following description and claims, and from reviewing the accompanying drawings.

BRIEF DESCRIPTION OF THE DRAWINGS

FIG. 5 is a diagrammatic representation of a system in accordance with another embodiment of the present invention.

DETAILED DESCRIPTION OF EMBODIMENTS OF THE INVENTION

Figure 1:
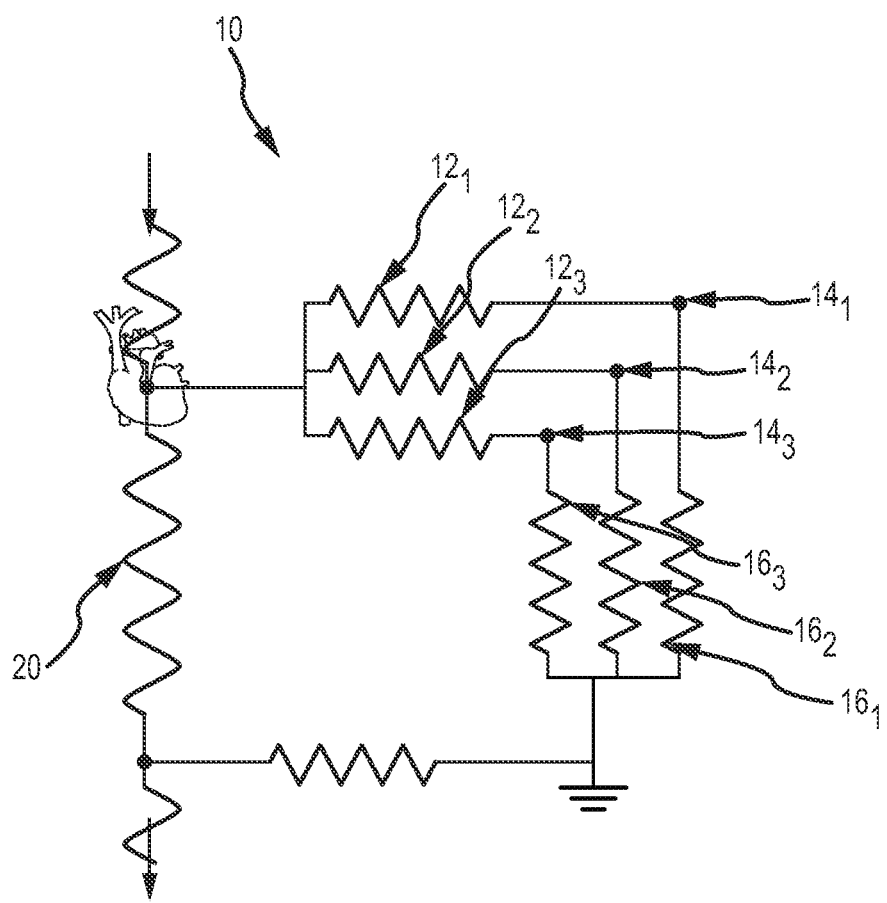
FIG. 1 is schematic diagram illustrating resistances in a circuit in a conventional medical position and navigation system.
Figure 2:
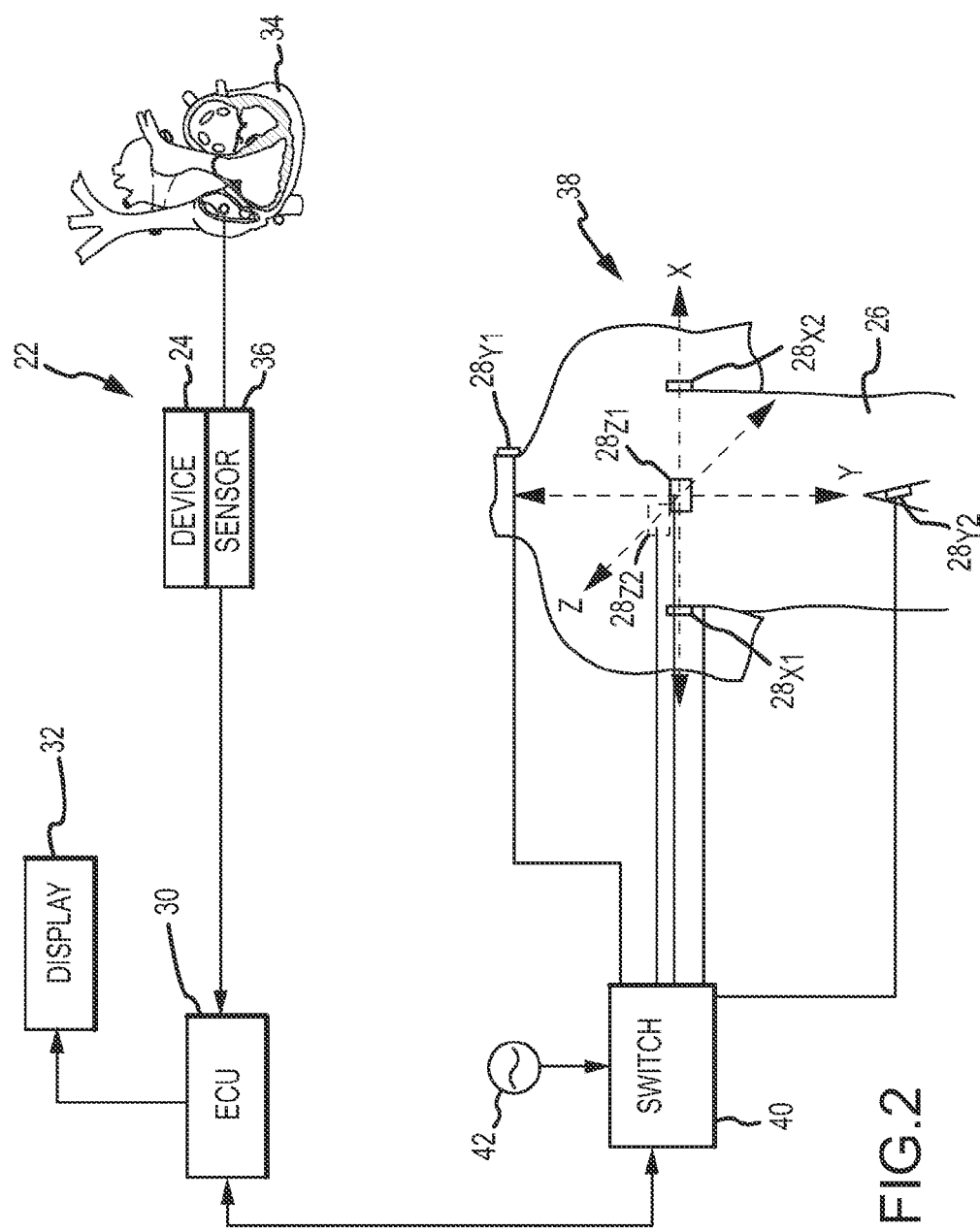
FIG. 2 is a diagrammatic view of a system in accordance with the present teachings.

Referring now to the drawings wherein like reference numerals are used to identify identical components in the various views, FIG. 2 illustrates one embodiment of a system 22 for determining the position of a medical device 24 in a body 26. System 22 may include a plurality of patch electrodes 28 applied to body 26, an electronic control unit (ECU) 30 and a display 32.

In the illustrated embodiment, system 22 is used to determine the position of medical device 24 within a heart 34. Medical device 24 may, for example, comprise a deformable catheter of the type used to allow removal of bodily fluids or injection of fluids and medicine into body 26 and/or for transporting surgical tools or instruments within body 16 including those use for pacing or tissue ablation of heart 34. The catheter may be manipulated manually by a clinician or automatically through, for example, robotic controls and may be inserted within a vessel located near the surface of a body (e.g., in an artery or vein in the leg, neck, or arm) in a conventional manner and maneuvered to a region of interest in body 26 such as heart 34 under the guidance of system 22. Device 24 may, for example, comprise an electrophysiology (EP) mapping catheter for use in gathering EP data associated with heart 34 to enable generation of an image of the geometry of the heart surface and related EP data. Device 24 may alternatively comprise an intracardiac echocardiography (ICE) catheter used to generate an image of a region of interest within body 26 such as heart 34. Device 24 may alternatively comprise an ablation catheter used to ablate tissue within heart 34 to treat abnormal heart rhythms such as atrial fibrillation, ventricular tachycardia and similar conditions. Although examples of specific medical devices 24 associated with diagnosis and treatment of conditions associated with heart 34 have been described, it should be understood that the inventive system 22 may find application in connection with determining the position of a variety of medical devices in varying locations within human and non-human bodies. Medical device 24 includes one or more position sensors 36. In the illustrated embodiment, positions sensors 36 are electrodes configured to generate an induced voltage responsive to the transmission of current by patch electrodes 28.

Patch electrodes 28 are provided to generate electrical signals used in determining the position of device 24 within a three dimensional coordinate system 38 of system 22. Electrodes 28 may also be used to generate EP data regarding heart 34. Electrodes 28 are placed orthogonally on the surface of body 26 and are used to create axes specific electric fields within body 26. Electrodes $28_{X1}$, $28_{X2}$ may be placed along a first (x) axis. Similarly, electrodes $28_{Y1}$, $28_{Y2}$ may be placed along a second (y) axis and electrodes $28_{Z1}$, $28_{Z2}$ may be placed along a third (z) axis. Each of the electrodes 28 may be coupled to a multiplex switch 40. ECU 30 is configured through appropriate software to provide control signals to switch 40 and thereby sequentially couple pairs of electrodes 28 to a signal generator 42. Excitation of each pair of electrodes 28 generates an electromagnetic field within body 26 and within an area of interest such as heart 34. Voltage levels at non-excited electrodes 28 may be filtered and converted and provided to ECU 30 for use as reference values.

Electronic control unit (ECU) 30 provides a means for controlling the operation of various components of system 22 including device 24, display 32 and switch 40. ECU 30 also provides a means for determining the position and orientation of medical device 24. ECU 30 may comprise a programmable microprocessor or microcontroller or may comprise an application specific integrated circuit (ASIC). ECU 30 may include a central processing unit (CPU) and an input/output (I/O) interface through which ECU 30 may receive a plurality of input signals including signals generated by device 24 (and particularly sensors 36) and patch electrodes 28 and generate a plurality of output signals including those used to control and/or provide data to device 24, display 32, and switch 40.

In operation, ECU 30 generates signals to control switch 40 and thereby selectively energize patch electrodes 28. ECU 30 receives position signals from position sensors 36 on device 24 reflecting changes in voltage levels on sensors 36 and from the non-energized patch electrodes 28. ECU 30 uses the raw location data produced by sensors 36 and electrodes 28 and corrects the data to account for respiration and other artifacts. ECU 30 then generates display signals to generate a display on display 32.

Display 32 is provided to convey information to a physician to assist in diagnosis and treatment. Display 32 may comprise a conventional computer monitor or other display device. Display 32 presents a graphical user interface (GUI) to the physician. The GUI may include a variety of information including, for example, an image of the geometry of heart 34, EP data associated with heart 34, graphs illustrating voltage levels over time for various electrodes, and images of medical device 24 and related information indicative of the position of device 24 relative to heart 34 and coordinate system 38.

As discussed hereinabove, conventional position and navigation systems based on the principal of passing electric currents through the thorax using electrodes 28 and measuring the resulting voltage drops on sensors 36 employ a reference electrode that is typically located near the stomach of body 26. The reference electrode serves as the origin of coordinate system 38 and the voltage measurements on sensors 36 are compared to the voltage at the reference electrode. In accordance with one embodiment of the present invention, the reference electrode is moved to a location on the surface of the body nearer heart 34. In yet another embodiment of the invention, a virtual reference electrode is established within body 26 and, preferably, within heart 34 as described hereinbelow.

Figure 3:
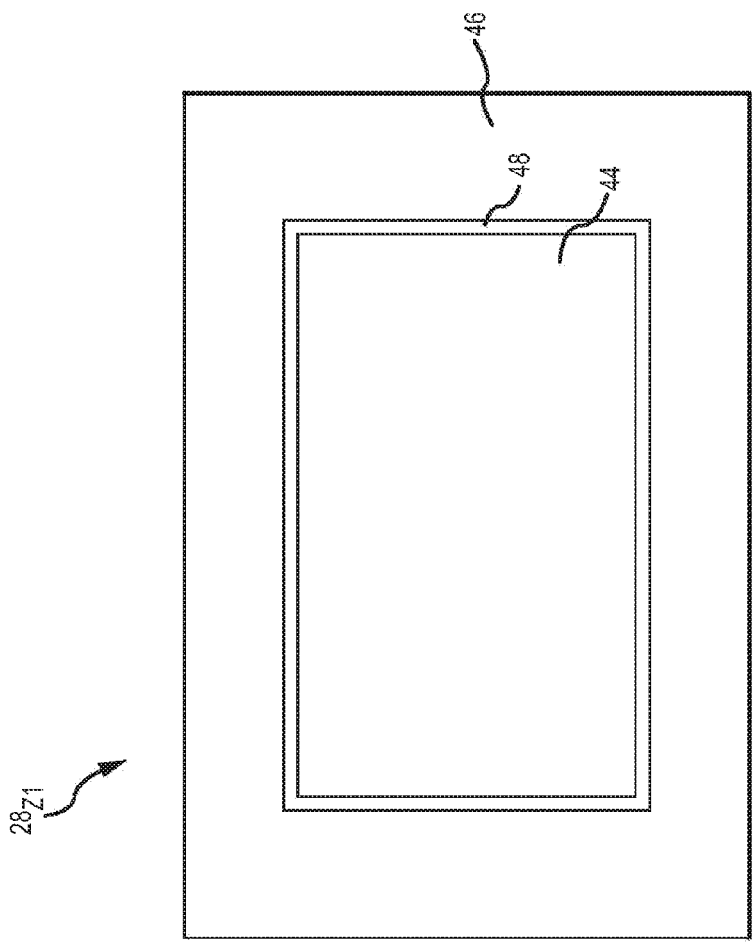
FIG. 3 is a diagrammatic representation of a patch in accordance with one embodiment of the present teachings.

Referring to FIG. 3, in accordance with one embodiment of the invention, at least one of the electrodes—in this case patch electrode $28_{Z1}$—is configured to perform multiple functions. In particular, patch electrode $28_{Z1}$ includes a device 44 comprising an electrode configured to establish an electrical pathway with another electrode (in this case $28_{Z2}$) disposed on an opposed surface of body 26. Electrode $28_{Z1}$ also includes a device 46 comprising an electrode configured to act as a reference electrode and output a reference signal against which the voltage measurements on position sensors 36 are compared. Devices 44 and 46 are electrically isolated from one another. In the illustrated embodiment, devices 44 and 46 are mechanically connected to one another through the support of a common flexible base layer with an electrical insulator 48 separating devices 44 and 46. It should be understood, however, that devices 44 and 46 need not be mechanically connected and could be mechanically separate with an air gap serving as an insulator between devices 44, 46. In the illustrated embodiment, device 46 surrounds device 44 and is concentric with device 44. In this manner, devices 44 and 46 have a common geometric center. It should be understood, however, that device 44 may alternatively be arranged to surround device 46. Further, it should be understood that, while preferable, devices 44, 46 need not be arranged so as to be concentric and having a common geometric center and that the benefits of the invention are achieved by moving the reference electrode (here device 46) nearer to heart 34 and the location of positions sensors 36. Accordingly, for example, devices 44, 46 may be arranged to be side by side with their geometric centers offset from one another. Finally, although patch electrode $28_{Z1}$ is shown as a multi-function patch in the illustrated embodiment, it should be understood that any of patches $28_{X1}$, $28_{X2}$, $28_{Y1}$, $28_{Y2}$, or $28_{Z2}$ could be configured in the same manner.

Figure 4:
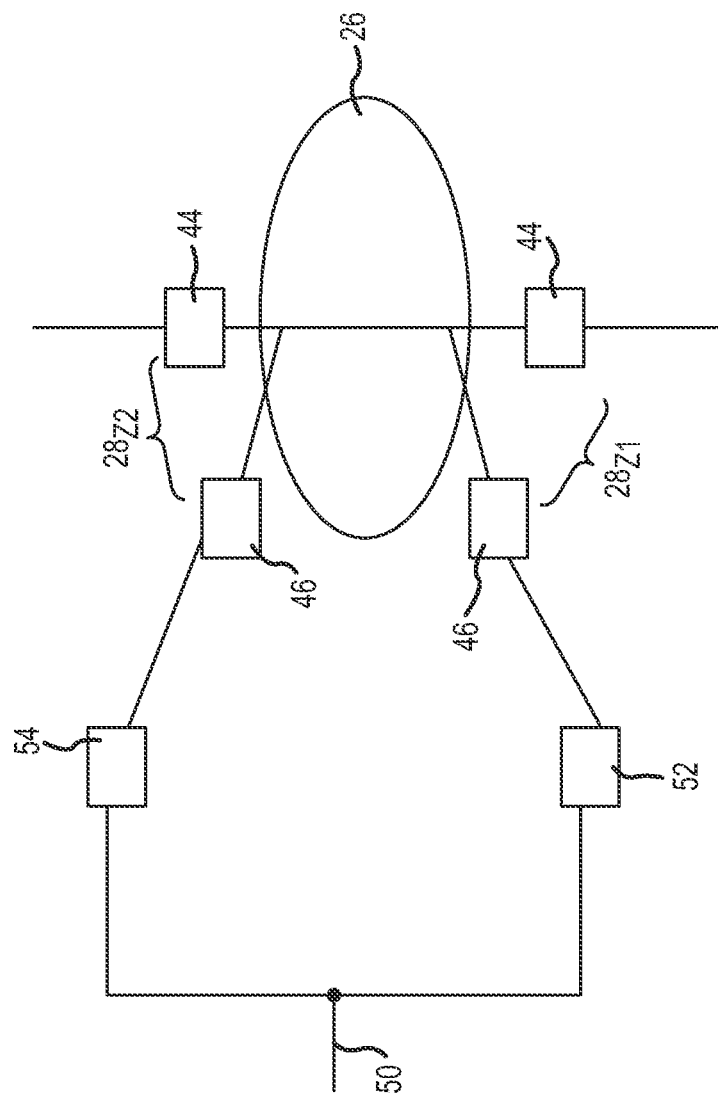
FIG. 4 is a schematic diagram illustrating a circuit coupling drive and reference electrodes to other components of a system in accordance with the present teachings.

Referring now to FIG. 4, in accordance with another embodiment of the invention both of patches $28_{Z1}$ and $28_{Z2}$ may be configured as multi-function patches as discussed hereinabove. The devices 46 serving as a reference electrode on each of patches $28_{Z1}$ and $28_{X2}$ are tied to a common reference node 50. In this manner a virtual reference electrode is established within body 26 nearer to heart 34 and position sensors 36 as opposed to remaining on the surface of body 26.

As a result, the origin of coordinate system 38 to which voltage measurements on sensors 36 are referenced is moved even closer to sensors 36 to further reduce position measurement errors. Devices 46 on patches $28_{Z1}$ and $28_{Z2}$ may be tied to reference node 50 through impedance devices 52, 54, respectively. Impedance devices may comprise a resistor or another conventional impedance device such as a capacitor or inductor. Impedance devices 52, 54 may have the same impedance value. Impedance devices 52, 54 preferably have different impedance values, however, to allow the virtual reference electrode and system origin to be located at a point other than the geometric center of a line connecting devices 46 of patches $28_{Z1}$ and $28_{Z2}$. The heart 34, for example, is typically located nearer the chest than the back. Accordingly, impedance device 52 may have a lower impedance value relative to device 54 to move the virtual reference electrode and system origin to a location nearer the chest. In yet another embodiment of the invention, impedance devices 52, 54 have variable impedance values. Impedance devices 52, 54 may, for example, comprise potentiometers or variable resistors or rheostats. In this configuration, impedance devices 52, 54 may be adjusted to establish a reference electrode and system origin in an appropriate location despite anatomical differences among humans or across species. A method for establishing the virtual reference electrode and system origin may, for example, include the steps of introducing a medical device 24 with a position sensor 36 into an anatomical region of interest and adjusting the impedance values on devices 52, 54 until the difference in voltages generated by position sensor 36 and output at reference node 50 and is at a predetermined minimum level such that the location of position sensor 36 is established as the virtual reference electrode and system origin. Although the illustrated embodiment shows patches $28_{Z1}$ and $28_{Z2}$ configured as multi function patches and used to establish the reference electrode, it should be understood that patch pairs $28_{X1}$ and $28_{X2}$ or $28_{Y1}$ and $28_{Y2}$ could alternatively be configured in the same manner. Further, multiple patch pairs could be configured in the same manner and collectively or individual (through, e.g., one or more switches controlled by ECU 30) to reference node 50 in order to establish a virtual reference electrode and system origin at a precise location along multiple axes.

A system in accordance with the above-identified embodiments of the invention represents an improvement relative to conventional systems. The inventive system locates the reference electrode serving as the origin of the navigation system's coordinate system 38 nearer to the anatomical region of interest, such as heart 34, and nearer to the position sensors 36 on medical device 24. Locating the reference electrode in this way reduces or eliminates the impact of the body's resistance on the position measurements and, particularly, in the inter axis variability of this resistance. Eliminating this resistance results in significant improvement in reducing or eliminating measurement errors due to drift resulting from a changing position of medical device 24 over time relative to the original measured position, shift resulting from a changes to certain parameters (e.g., connection or disconnection of medical device 24 or movement of the reference electrode, scatter resulting from variation of impedance among position sensors 36 and related circuitry and offset resulting from differences in impedance among the position sensors 36 and related circuitry among different devices 24. In the case of scatter for example, and with reference to equation (1) hereinabove, differences in impedance among individual electrodes will result in different determinations of electrode position even if the electrodes are actually located in the same position within the coordinate system 38. A reduction in body resistance, however, will cause a proportion reduction in the position values for the two electrodes and reduce the overall error in the measured difference in positions.

As discussed hereinabove, in one embodiment of the invention devices 44, 46 are integrated and supported on a common base layer of a patch electrode 28 affixed to the surface of body 26. Referring to FIG. 5, in another aspect of the present invention, this concept can be extended to permit the integration of additional or different components and functions and use with other types of position and navigation systems. As shown in FIG. 5, a system 56 for determining the position of a medical device 24 within a body 26 in accordance with another embodiment of the invention includes a field generator 58, a position sensor 60, a patch 62 affixed to the surface of body 26 and an electronic control unit (ECU) 64.

Field generator 58 generates an electrical and/or magnetic field used in determining the position of device 24 and navigating device 24. Field generator 58 may comprise an electric field generator as described hereinabove in system 22 in which electric currents are directed from a signal generator 42 through patch electrodes 28. Alternatively, field generator 58 may comprise a magnetic field generator such as those in the systems sold under the trademarks "GMPS™" by Mediguide Ltd. or "CARTO™" by Biosense Webster, Inc.

Position sensor 60 generates a position signal indicative of a position of medical device 24 in a coordinate system 78 of system 56. Sensor 60 may be mounted on device 24. Alternatively, sensor 60 may be physically separate from device 24 and offset from device 24 at a fixed distance. In any event, sensor 60 has a known positional relationship to device 24 such that the output of sensor 60 is indicative of the position of device 24. The type of position sensor 60 employed will depend on the type of field generator 58. If the field generator 58 is an electric field generator as in system 22, position sensor 60 may comprise a conventional electrode. If the field generator 58 is a magnetic field generator, position sensor 60 may comprise a conventional coil on which a current is induced. Sensor 60 will generate a voltage and/or current that is indicative of the position of sensor 60 and device 24 and provide a corresponding position signal to ECU 64. Although position sensor 60 is shown on or near device 24 in the illustrated embodiment while field generator 58 is disposed outside of the body, it should be understood that these roles may be reversed with field generator 58 within body 26 in a known positional relationship relative to device 24 and position sensor 60 disposed outside of body 26.

Patch 62 is used to affix various components of system 56 to body 26 and may perform a plurality of functions as described below. Patch 62 includes a base layer 66 and multiple devices such as devices 68, 70, 72, 74 configured to perform different functions and electrically isolated from one another on patch 62.

Base layer 66 comprises a flexible and unitary structure on which devices 68, 70, 72, 74 are supported. Base layer 66 is conventional in the art and may be made from conventional materials such as polytetrafluoroethylene (PTFE). Base layer 66 may be made from an electrically conductive material and may include an adhesive on one side configured to allow base layer 66 to attach and adhere to the external surfaces of body 26. Base layer 66 may also include insulation separating devices 68, 70, 72, 74 from one another to electrically isolate devices 68, 70, 72, 74.

Devices 68, 70, 72, 74 may be configured to provide a variety of functions. In accordance with the present invention, one or more of devices 68, 70, 72, 74 generate an output that is used by ECU 64 together with the position signal generated by position sensor 60 to determine the position of position sensor 60 and device 24. As discussed hereinabove, devices 68 and 70 may (similar to devices 44, 46) comprise electrodes configured to establish an electrical pathway with another electrode disposed on an opposed surface of body 26 and configured to output a reference signal against which the position signal from sensor 60 is compared, respectively. Devices 72, 74 may perform additional functions relied upon in assessing the position of sensor 60 and/or providing additional information regarding system 22. Device 72, for example, may comprise an electrode configured to detect electrical activity in heart 34 (i.e. an ECG electrode). This information can be used to compensate for change s in position of sensor 60 due to movement of heart 34 and/or to provide information regarding electrical activity of heart 34. Device 74 may comprise a position sensor for detecting movement of body 26. In the case where field generator 58 is a magnetic field generator, for example, device 74 may comprise a coil whose output is indicative of a change in position of the body within the generated magnetic field such as the body position sensor used in the magnetic position and navigation system sold under the trademark "GMPS" by Mediguide, Ltd. This information can be used to compensate for change in position of sensor 60 due to movement of body 26 relative to the generated magnetic field.

Although patch 62 is shown in the illustrated embodiment with four devices 68, 70, 72, 74, it should be understood that the number and type of devices employed on patch 62 will depend on the nature of the position and navigation system employed. For example, patch 62 may include only devices 72, 74 if a magnetic position and navigation system is used while patch 62 may include devices 68, 70, 72 if a system such as system 22 is used.

ECU 64 provides a means for controlling the operation of various components of system 56 including device 24, display 32 and field generator 58. ECU 64 also provides a means for determining the position and orientation of medical device 24. ECU 64 may comprise a programmable microprocessor or microcontroller or may comprise an application specific integrated circuit (ASIC). ECU 64 may include a central processing unit (CPU) and an input/output (I/O) interface through which ECU 64 may receive a plurality of input signals including signals generated by device 24 (and particularly sensors 60) and devices 68, 70, 72, 74 on patch 62 and generate a plurality of output signals including those used to control and/or provide data to device 24, display 32, and field generator 58.

In operation, ECU 64 generates signals to control field generator 58. ECU 64 receives position signals from position sensors 60 on device 24 reflecting changes in voltage or current levels on sensors 60 and other sensors within system 56. ECU 64 uses the raw location data produced by sensors 60 and corrects the data to account for respiration and other artifacts. ECU 64 then generates display signals to generate a display on display 32.

A system 56 for determining a position of medical device 24 within body 26 is advantageous relative to conventional systems because it integrates component and/or functions that are separate in conventional systems. As a result, fewer components are required for procedures thereby reducing inventory and procedural time and complexity.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for determining a position of a medical device within a body, said system defining a coordinate system and comprising:
    a field generator;
    a first position sensor generating a position signal indicative of a three-dimensional position of said medical device in said coordinate system, one of said field generator and said first position sensor disposed outside of said body and another of said field generator and said first position sensor having a known positional relationship to said medical device;
    a first patch comprising:
        a flexible and unitary base layer configured for attachment to an external surface of said body;
        a first device supported on said base layer and configured to perform a first function; and
        a second device supported on said base layer and configured to perform a second function different from said first function, said second device electrically isolated from said first device;
    a second position sensor comprising a coil and wherein the first patch is configured to support the coil, and wherein the coil is configured such that a current is induced within the coil when exposed to a magnetic field; and,
    an electronic control unit configured to determine said three-dimensional position of said medical device responsive to said position signal and an output of at least one of said first and second devices,
    wherein said second device comprises an electrode configured to establish an electrical pathway with another electrode disposed on a surface of said body.

2. The system of claim 1, wherein said first device comprises a third position sensor configured to detect movement of said body.

3. The system of claim 1, wherein said second device comprises an electrode configured to detect electrical activity in a heart of said body.

4. The system of claim 1, wherein said second device comprises an electrode configured to output a reference signal against which said position signal is compared.

5. The system of claim 1, wherein said patch further includes a third device supported on said base layer and configured to perform a third function different from said first and second functions, said third device electrically isolated from said first and second devices.

6. The system of claim 1, wherein one of said first and second devices surrounds another of said first and second devices.

7. The system of claim 6, wherein said first and second devices are concentrically arranged.

8. The system of claim 1, wherein a geometric center of said first device is offset from a geometric center of said second device.

9. The system of claim 1, further comprising an impedance device coupled to the first patch, the impedance device configured to allow the electronic control unit to create a virtual reference electrode at a desired distance from the first patch.

10. A system for determining a position of a medical device within a body, said system defining a coordinate system and comprising:
   a field generator;
   a first position sensor generating a position signal indicative of a three-dimensional position of said medical device in said coordinate system, one of said field generator and said first position sensor disposed outside of said body and another of said field generator and said first position sensor having a known positional relationship to said medical device;
   a patch electrode comprising:
      a flexible base layer configured for attachment to an external surface of said body;
      a first electrode supported on said base layer, said first electrode configured to generate an electrical signal; and,
      a second electrode supported on said base layer, said second electrode configured to establish an origin of the coordinate system and to generate a reference signal;
   a second position sensor comprising a coil and wherein the coil is configured to couple to the patch electrode, and wherein the coil is configured such that a current is induced within the coil when exposed to a magnetic field; and,
   an electronic control unit configured to determine said three-dimensional position of said medical device responsive to said position signal and said reference signal.

11. A system for determining a position of a medical device within a body, said system defining a coordinate system and comprising:
   a field generator;
   a first position sensor generating a position signal indicative of a three-dimensional position of said medical device in said coordinate system, one of said field generator and said first position sensor disposed outside of said body and another of said field generator and said first position sensor having a known positional relationship to said medical device;
   a patch electrode comprising:
      a flexible base layer configured for attachment to an external surface of said body;
      a first electrode supported on said base layer and configured to establish an electrical pathway with another electrode disposed on a second external surface of the body opposite the first external surface and to generate an electric field within the body; and,
      a second position sensor comprising a coil and wherein the coil is configured to couple to the patch electrode, and wherein the coil is configured such that a current is induced within the coil when exposed to a magnetic field; and,
   an electronic control unit configured to determine said three-dimensional position of said medical device responsive to said position signal and said reference signal.

12. The system of claim 11, wherein said base layer includes an adhesive on a first side configured for coupling to said first surface of said body.

13. The system of claim 11, wherein said base layer is unitary in construction.

14. The system of claim 11, further comprising a second electrode and wherein said first and second electrodes are electrically isolated from one another.

15. The system of claim 11, further comprising a second electrode and wherein one of said first and second electrodes surrounds another of said first and second electrodes.

16. The system of claim 15, wherein said first and second electrodes are concentrically arranged.

17. The system of claim 11, further comprising a second electrode and wherein a geometric center of said first electrode is offset from a geometric center of said second electrode.

18. The system of claim 11, further comprising a second position sensor supported on said base layer, said position sensor configured to detect movement of the body.

* * * * *